(12) United States Patent
Koizumi et al.

(10) Patent No.: US 10,573,009 B2
(45) Date of Patent: Feb. 25, 2020

(54) IN VIVO MOVEMENT TRACKING APPARATUS

(71) Applicants: The University of Tokyo, Bunkyo-ku, Tokyo (JP); The University of Electro-Communications, Chofu-shi, Tokyo (JP); Public University Corporation Yokohama City University, Yokohama-shi, Kanagawa (JP)

(72) Inventors: Norihiro Koizumi, Chofu (JP); Atsushi Kayasuga, Tokyo (JP); Kyohei Tomita, Chofu (JP); Izumu Hosoi, Chofu (JP); Yu Nishiyama, Chofu (JP); Hiroyuki Tsukihara, Tokyo (JP); Hideyo Miyazaki, Tokyo (JP); Hiroyuki Fukuda, Yokohama (JP); Kazushi Numata, Yokohama (JP); Kiyoshi Yoshinaka, Tsukuba (JP); Takashi Azuma, Kawaguchi (JP); Naohiko Sugita, Tokyo (JP); Yukio Homma, Tokyo (JP); Yoichiro Matsumoto, Tokyo (JP); Mamoru Mitsuishi, Tokyo (JP)

(73) Assignees: THE UNIVERSITY OF TOKYO, Tokyo (JP); THE UNIVERSITY OF ELECTRO-COMMUNICATIONS, Tokyo (JP); PUBLIC UNIVERSITY CORPORATION YOKOHAMA CITY UNIVERSITY, Kanagawa (JP)

( * ) Notice: Subject to any disclaimer, the term of this patent is extended or adjusted under 35 U.S.C. 154(b) by 97 days.

(21) Appl. No.: 15/876,233

(22) Filed: Jan. 22, 2018

(65) Prior Publication Data
US 2018/0253855 A1 Sep. 6, 2018

(30) Foreign Application Priority Data

Mar. 3, 2017 (JP) ................................. 2017-040348

(51) Int. Cl.
*G06K 9/00* (2006.01)
*G06T 7/207* (2017.01)
(Continued)

(52) U.S. Cl.
CPC .............. *G06T 7/207* (2017.01); *A61B 5/004* (2013.01); *G06T 7/0016* (2013.01); *G06T 7/149* (2017.01); *G06T 2211/40* (2013.01)

(58) Field of Classification Search
CPC . G06T 2207/20116; G06T 2207/30084; G06T 2207/30096; G06T 7/0012; G06T 7/149
See application file for complete search history.

(56) References Cited

U.S. PATENT DOCUMENTS 5,553,618 A * 9/1996 Suzuki ..................... A61N 7/02
600/411
5,722,411 A * 3/1998 Suzuki ..................... A61N 7/02
600/439

(Continued)

FOREIGN PATENT DOCUMENTS

JP H07-47079 A 2/1995

OTHER PUBLICATIONS

Qin, Xianjing, et al. "Partial sparse shape constrained sector-driven bladder wall segmentation." Machine Vision and Applications 26.5 (2015): 593-606. (Year: 2015).*

(Continued)

*Primary Examiner* — Avinash Yentrapati
(74) *Attorney, Agent, or Firm* — HEA Law PLLC

(57) ABSTRACT

Provided is an in vivo movement tracking apparatus configured to track a portion of interest that moves in vivo, in
(Continued)

which accuracy and robustness of tracking are improved. The apparatus is configured to determine an estimated position of ah organ in a biological image based on the past movement of the organ and search for contour points corresponding to a plurality of control points, respectively, representing a contour shape of the organ in a region corresponding to the estimated position, to thereby determine an estimated contour of the organ based on the contour points. The in vivo movement tracking apparatus is configured to determine a position of a portion of interest, which moves in association with the organ, based on the estimated contour with reference to previously acquired sample data regarding a positional relationship between a contour of the organ and the portion of interest.

3 Claims, 9 Drawing Sheets

(51) Int. Cl.
*G06T 7/149* (2017.01)
*G06T 7/00* (2017.01)
*A61B 5/00* (2006.01)

(56) References Cited

U.S. PATENT DOCUMENTS

| | | | | |
|---|---|---|---|---|
| 2008/0015428 | A1* | 1/2008 | Epstein | G06T 7/215 600/410 |
| 2008/0292169 | A1* | 11/2008 | Wang | G06T 7/0012 382/131 |
| 2010/0166275 | A1* | 7/2010 | Liu | G06K 9/6207 382/131 |
| 2012/0275659 | A1* | 11/2012 | Gomas | G06K 9/6209 382/110 |
| 2013/0057547 | A1* | 3/2013 | Hwang | G06T 17/00 345/420 |
| 2015/0003697 | A1* | 1/2015 | Beymer | G06T 7/0012 382/128 |
| 2015/0051480 | A1* | 2/2015 | Hwang | A61B 8/08 600/424 |
| 2015/0078640 | A1* | 3/2015 | Guo | G06T 7/11 382/131 |

OTHER PUBLICATIONS

Yan, Pingkun, et al. "Discrete deformable model guided by partial active shape model for TRUS image segmentation." IEEE Transactions on Biomedical Engineering 57.5 (2010): 1158-1166. (Year: 2010).*

P. Yan et al., "Discrete Deformable Model Guided by Partial Active ShapeModel for TRUS Image Segmentation", IEEE Transactions on BiomedicalEngineering, vol. 57, pp. 1158-1166, 2010.

* cited by examiner

IN VIVO MOVEMENT TRACKING APPARATUS

CROSS-REFERENCE TO RELATED APPLICATION

The present application claims priority from Japanese application JP 2017-040348 filed on Mar. 3, 2017, the content of which is hereby incorporated by reference into this application.

BACKGROUND OF THE INVENTION

1. Field of the Invention

The present invention relates to an in vivo movement tracking apparatus configured to track a portion of interest that moves in vivo.

2. Description of the Related Art

There has been known high-intensity focused ultrasound (HIFU) for treating cancer, a tumor, and the like by burning the cancer, the tumor, and the like with a high-intensity focused ultrasonic wave (see Japanese Patent Application Laid-open No. H 07-47079). For example, an apparatus for treating a calculus, prostate cancer, and liver cancer, which adopts HIFU, has been developed and used.

In HIFU therapy, in order to prevent normal tissues and the like other than treatment areas (affected parts), for example, a calculus, cancer, and a tumor, from being damaged, it is desired that the position of a treatment area be grasped so that a high-intensity ultrasonic wave be focused on the position. Therefore, there has hitherto been used, for example, a system configured to confirm the position of a treatment area through use of magnetic resonance imaging (MRI) or an ultrasonic image for diagnosis and simultaneously focus an ultrasonic wave for treatment on the position.

SUMMARY OF THE INVENTION

However, most of body parts (organs) in vivo may move along with breathing or cardiac pulsation, and an affected part being a portion of interest, also moves in association with an organ. It has been reported that, in particular, the liver moves by from 10 mm to 20 mm or more at a maximum speed of from 15 mm/sec to 20 mm/sec along with breathing and may move by 100 mm or more along with deep breathing. It has also been reported that the kidney moves by from 5 mm to 9 mm on average along with breathing. With HIFU therapy of, for example, a calculus, cancer, and a tumor that occur in the kidney, the liver, and the like, it is difficult to accurately irradiate an organ with an ultrasonic wave while following the movement of the organ in vivo, and hence the movement of the organ is a major obstacle for treatment.

Specifically, a method of directly following an affected part in an image has, for example, the following problems. Specifically, changes in brightness and shape of the affected part caused by HIFU therapy makes it difficult to follow the affected part. Further, the feature amount of the affected part in an image is often small, and hence it is difficult to ensure accuracy and robustness of following.

Meanwhile, there is a method involving tracking an organ with respect to an affected part that moves in association with the organ and grasping the position of the affected part through use of the positional relationship between the organ and the affected part. Specifically, it has been proposed that the position of the organ be grasped through template matching using a template of the organ in an image.

However, the movements of the kidney and the liver cause a change in relative positional relationship with respect to the rib, the lung, the heart, the gallbladder, and the fascia on the periphery of the organs, and deformation of the organs. With this, a significant change occurs in an image, for example, an ultrasonic image pattern that captures an organ having an affected part. A change in the image reduces, for example, similarity between the template of the organ and the image in tracking through template matching, leading to a failure of tracking. In particular, in an ultrasonic image, for example, an acoustic shadow caused by the rib, a calculus, or the like and shielding caused by the lung occur as artifacts. When the template overlaps with a portion of an organ that is shielded by an acoustic shadow or the like, matching accuracy decreases, resulting in a decrease in accuracy of following of an organ and further a decrease in accuracy of following of an affected part.

Further, due to the deformation and rotation of an organ associated with the movement of the organ, the positional relationship between the organ and an affected part also changes. The change in positional relationship also causes a decrease in accuracy of following of the affected part.

The movement of a body part in vivo also causes a problem in therapeutic methods other than HIFU therapy, for example, a surgical operation for the heart and radiation therapy for lung cancer.

The present invention provides an in vivo movement tracking apparatus configured to suitably track a portion of interest that moves in vivo.

(1) According to one embodiment of the present invention, there is provided an in vivo movement tracking apparatus including: at least one processor; and at least one storage device configured to store a plurality of instructions, the plurality of instructions causing, when being executed by the at least, one processor, the at least one processor to perform: organ position estimation processing for determining an estimated position of an organ of concern in a biological linage, which is obtained by photographing a biological structure, based on a past movement of the organ of concern in vivo; contour estimation processing for searching for contour points of the organ of concern in a region corresponding to the estimated position in the biological image and determining an estimated contour of the organ of concern based on the contour points; and portion-of-interest tracking processing for determining a position of a portion of interest, which moves in association with the organ of concern, in the biological image based on the estimated contour with reference to previously acquired sample data regarding a positional relationship between a contour of the organ of concern and the portion of interest. The contour estimation processing includes: searching for the contour points corresponding to a plurality of control points, respectively, in an active contour model having a contour shape of the organ of concern; and determining the estimated contour by using a shape model representing the contour shape with a sum of a reference shape and a linear combination of a plurality of deformation modes that are linearly independent from each other, and a clear contour point having a degree of reliability greater than or equal to a predefined reference among the contour points. The estimated contour being determined by alternately repeating PASM processing and processing for correcting a position of the control point given by the PASM processing, with using the clear contour point as an initial value. The PASM processing determines a coefficient of each of the plurality of deformation modes in the linear combination based only on the control point corresponding to the clear contour point among the plurality of control points. The correction processing corrects the position of the control point given by the PASM processing by a SNAKE method, which is based on an energy minimizing principle regarding the contour shape.

(2) In the in vivo movement tracking apparatus according to Item (1), the portion-of-interest tracking processing can determine the position of the portion of interest corresponding to the estimated contour through use of a position model representing the position of the portion of interest corresponding to a contour of interest of the organ of concern with a sum of a reference position and a linear combination of a plurality of displacement modes corresponding to the plurality of deformation modes. Regarding the position model, an average position of the portion of interest, which is based on the sample data, can be set as the reference position, and the coefficient in the linear combination of each of the plurality of deformation modes in the shape model corresponding to the contour of interest can foe set as a coefficient in the linear combination of each of the plurality of displacement modes. The plurality of displacement modes can be determined, by applying the position model, in which the reference position and the coefficient in the linear combination are defined in this manner, to the sample data.

(3) In the in vivo movement tracking apparatus according to Item (1) and (2), the contour estimation processing can predict the contour at the estimated position based on the estimated contour in the past and search for the contour points along a direction orthogonal to the predicted contour.

(4) In the in vivo movement tracking apparatus according to Items (1) to (3), the at least, one storage device can further store: the biological image; and a plurality of instructions for causing, when being executed by the at least one processor, the at least one processor to perform: region-to-be-complemented setting processing for distinguishing a clear region having a clear image quality from an unclear region having an unclear image quality based on a predetermined criteria in an image of the organ of concern appearing on the biological image and determining a region to be complemented, which is formed of at least one polygon containing the unclear region and having the control points as vertices; and image synthesis processing for reading out, from the at least one storage device, the biological image in a polygon that is contained in the clear region and has, as vertices, the control points common to the control points of the at least one polygon in the region to be complemented, and subjecting the read biological image in the polygon to linear transformation to match the read biological image in the polygon to the at least one polygon in the region to be complemented, to thereby synthesize the biological image subjected to the linear transformation with the region to be complemented.

DETAILED DESCRIPTION OF THE INVENTION

Figure 1:
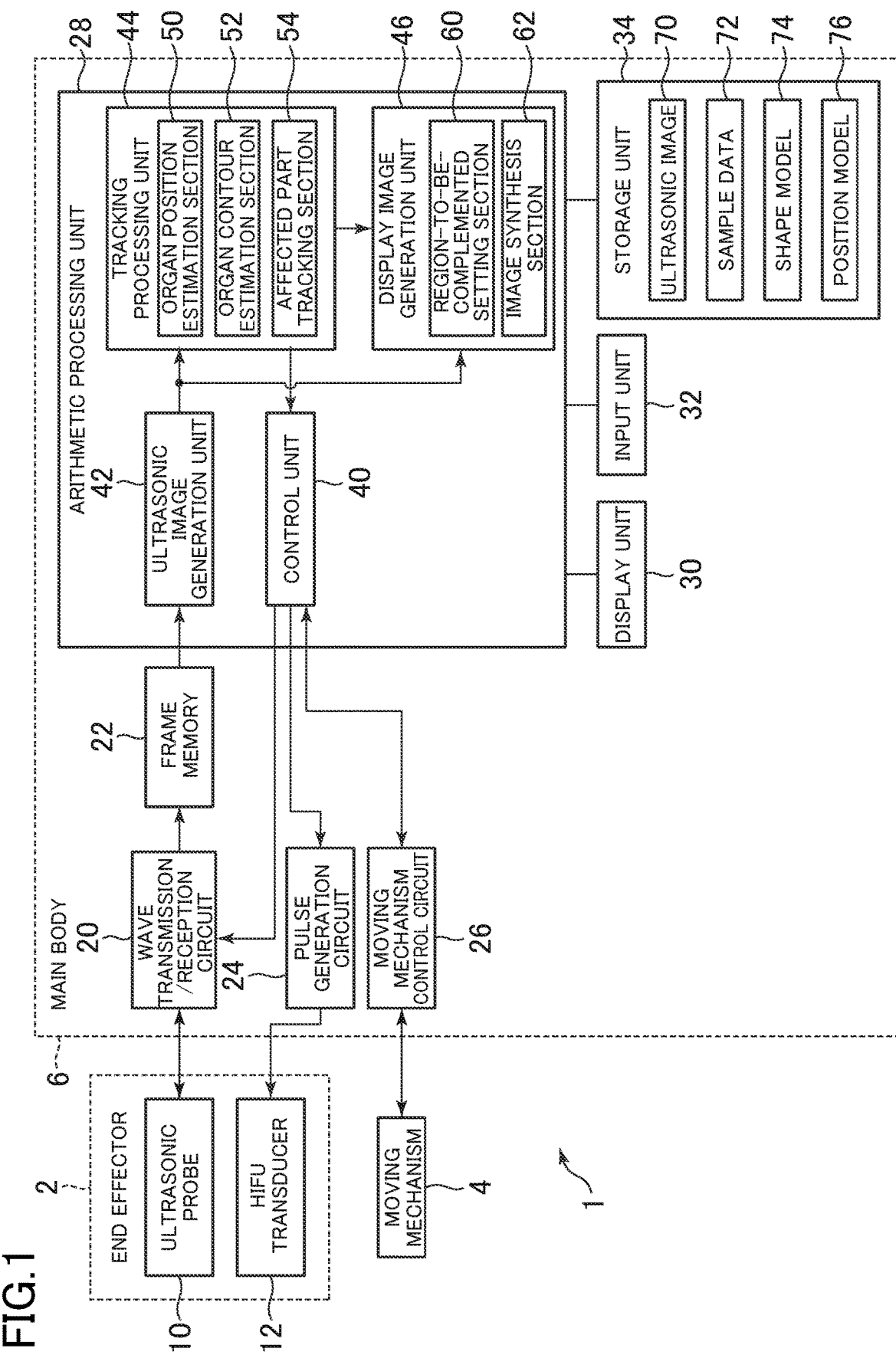
FIG. 1 is a block diagram for illustrating a schematic configuration of an ultrasound theragnostic system in an embodiment of the present invention.

Now, an in vivo movement tracking apparatus according to an embodiment of the present invention is described in detail referring to the drawings. The in vivo movement tracking apparatus is an apparatus configured to track a portion of interest that moves in association with an organ moving almost periodically in vivo in a biological image obtained by photographing a biological structure. Here, an organ attracting concern (organ of concern) as a target for observation or tracking is assumed as, for example, the kidney or the liver. As described above, the kidney and the liver move almost periodically in response to breathing of a living body of a subject to be examined, a patient, or the like (hereinafter referred to as "subject to be examined"). Further, the portion of interest is typically an affected part, for example, a calculus, cancer, or a tumor.

FIG. 1 is a block diagram for illustrating a schematic configuration of an ultrasound theragnostic system 1 of the embodiment. The ultrasound theragnostic system 1 includes an end effector 2, a moving mechanism 4, and a device main part 6, and further includes an in vivo movement tracking apparatus according to the present invention. The end effector 2 includes an ultrasonic probe 10 and an HIFU transducer 12 and is arranged so as to face a portion to be paid attention to (site of interest) in vivo, for example, the organ of concern or the affected part. The ultrasound theragnostic system 1 can capture an ultrasonic image as a biological image in real time with the ultrasonic probe 10, and the device main part 6 is configured to track the position of the portion of interest through use of the ultrasonic image. The moving mechanism 4 is controlled by the device main part 6 and is configured to three-dimensionally move the end effector 2 while following the position of the portion of interest. The ultrasound theragnostic system 1 enables monitoring and diagnosis of the organ and the portion of interest that moves in association with the organ by generating and displaying a display image through use of an ultrasonic tomographic image obtained by the ultrasonic probe 10 while performing processing of tracking the affected part. The ultrasound theragnostic system 1 can also treat the affected part through use of the HIFU transducer 12 in a non-invasive manner by HIFU therapy.

Figure 2:
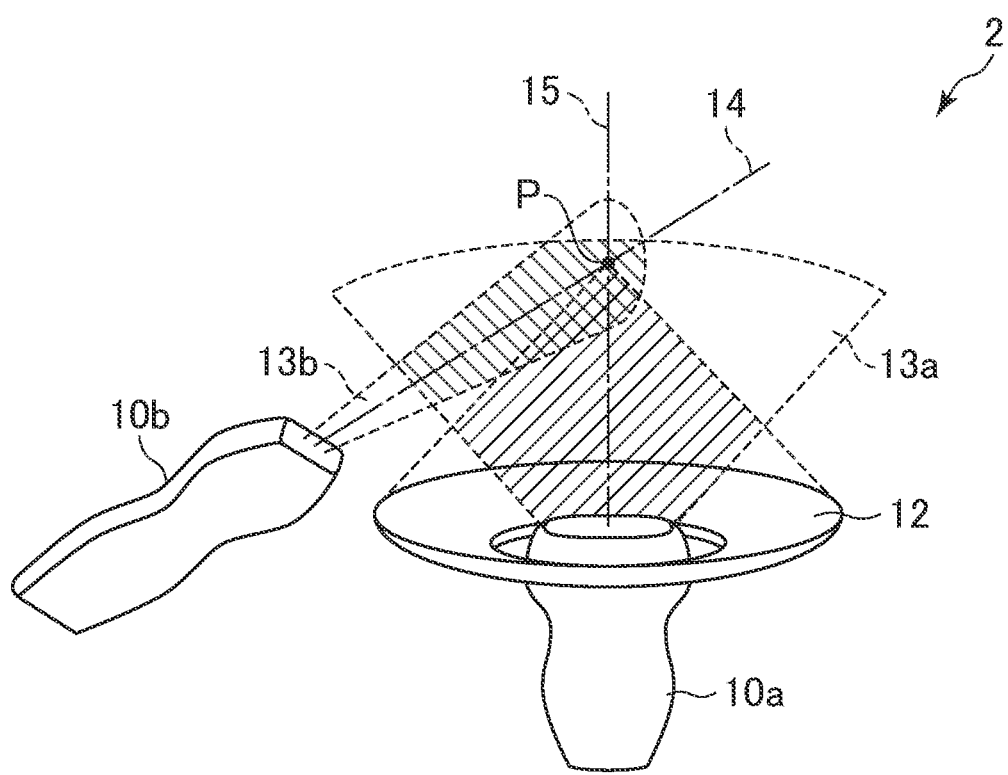
FIG. 2 is a schematic perspective view of an end effector to be used in the ultrasound theragnostic system in the embodiment of the present invention.

FIG. 2 is a schematic perspective view of the end effector 2. The ultrasonic probe 10 is configured to transmit an ultrasonic pulse and. receive a wave of an echo. Specifically, the ultrasonic probe IG includes an oscillator array, and forms an ultrasonic beam with the oscillator array and transmits the ultrasonic beam into a body of the subject to be examined. The ultrasonic beam is electronically scanned along the direction of the array. The ultrasonic beam is transmitted in a pulse form. The oscillator array transmits the ultrasonic beam and thereafter receives a wave of an echo from the body. In order to acquire three-dimensional information on the site of interest and to be adaptable to the three-dimensional movement of the sits of interest in the body, two ultrasonic probes 10a and 10b are arranged in the end effector 2 so that scanning surfaces 13a and 13b thereof are basically orthogonal to each other. With this, an ultrasonic biplane image is acquired as a biological image in which the structure of a body part or the like in vivo appears.

The HIFU transducer 12 is configured to generate a focused ultrasonic wave for HIFU therapy. For example, the HIFU transducer 12 includes an oscillator array arranged so as to surround the ultrasonic probe 10a in an annular shape, and the oscillator array forms a concave surface when viewed from the direction of ultrasonic wave transmission. The positional relationship between the ultrasonic probes 10a and 10b and the HIFU transducer 12 is basically set so that a focal point of the focused ultrasonic wave is positioned at an intersection P between a line of intersection 14 of the two scanning surfaces 13a and 13b of the ultrasonic probe 10 and a center axis 15 of an annular region of the oscillator array of the HIFU transducer 12.

Figure 3:
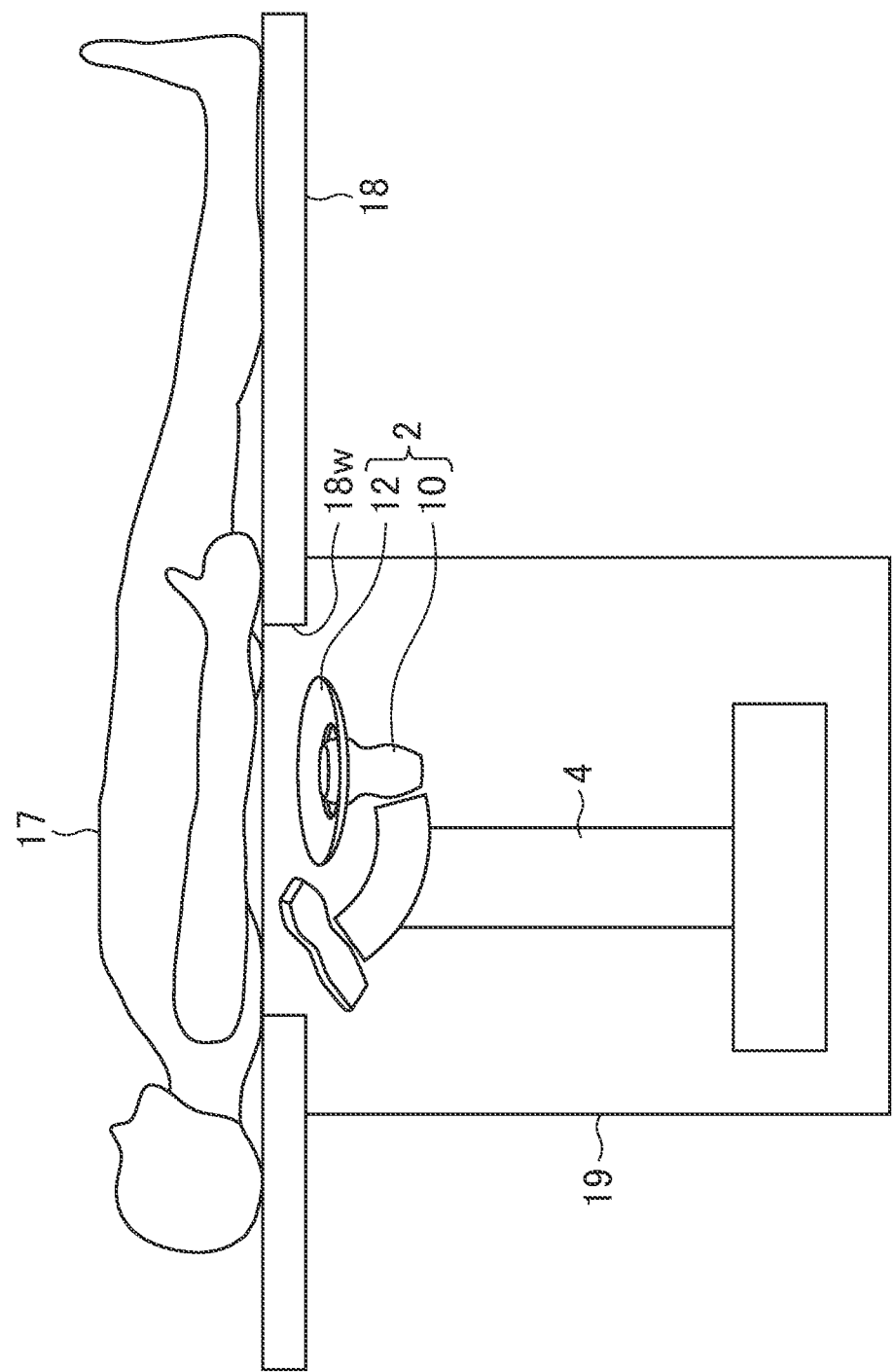
FIG. 3 is a schematic view of the ultrasound theragnostic system in the embodiment of the present invention.

FIG. 3 is a schematic view or the ultrasound theragnostic system 1 for illustrating an example of a configuration of an apparatus configured to perform, diagnosis and treatment with respect to, for example, a trunk portion or the subject to be examined. FIG. 3 is a schematic vertical sectional view in which a water tank 19 is arranged below a bed 18 on which a subject 17 to be examined lies down. The skin of a site to be diagnosed and treated of the subject 17 to be examined is brought into contact with a water surface of the water tank 19 through an opening 18w formed in the bed 18. Meanwhile, the end effector 2 is arranged in the water of the water tank 19. With this, the subject 17 to be examined and the end effector 2 are acoustically coupled to each other through the water. The end effector 2 can three-dimensionally move in the water with the moving mechanism 4.

The ultrasonic probe 10 and the HIFU transducer 12 transmit ultrasonic waves in accordance with drive signals from the device main part 6, and a reception signal obtained by the ultrasonic probe 10 is transmitted to the device main part 6. Transmission and reception of waves by the two ultrasonic probes 10a and 10b, and irradiation of an ultrasonic wave by the HIFU transducer 12 are performed in time division with a control unit 40. With this, interference of the ultrasonic waves can be avoided.

The device main part 6 includes a wave transmission/reception circuit 20, a frame memory 22, a pulse generation circuit 24, a moving mechanism control circuit 26, an arithmetic processing unit 28, a display unit 30, an input unit 32, and a storage unit 34. The device main part 6 and each unit thereof are not necessarily required to be a single apparatus and may be separated into a plurality of apparatus.

The arithmetic processing unit 28 includes, for example, processors such as a central processing unit (CPU), or processing circuits and peripheral circuits thereof. The arithmetic processing unit 28 is operated based on programs (source code or machine code) stored in the storage unit 34 and functions as the control unit 48, an ultrasonic image generation unit 42, a tracking processing unit 44, and a display image generation unit 46. The tracking processing unit 44 has functions as an organ position estimation section 50, an organ contour estimation section 52, and an affected part tracking section 54, and the display image generation unit 46 has functions as a region-to-be-complemented setting section 60 and an image synthesis section 62.

The wave transmission/reception circuit 20 is configured to transmit an ultrasonic wave from the ultrasonic probe 10 into the body and process an echo signal received by the ultrasonic probe 10 in accordance with the control by the control unit 40. At the time of transmission, the wave transmission/reception circuit 20 generates a transmission pulse for exciting and driving each oscillator of the oscillator array and outputs the transmission pulse to the ultrasonic probe 10. The wave transmission/reception circuit 20 adjusts a delay amount given to the transmission pulse for each oscillator to control the oscillation timing of each oscillator so that the ultrasonic wave transmitted from the ultrasonic probe 10 forms a transmission beam in a desired direction.

Meanwhile, at the time of reception, the wave transmission/reception circuit 20 receives a reception signal for each of the plurality of oscillators forming the oscillator array from the ultrasonic probe 10. The wave transmission/reception circuit 20 amplifies the reception signal obtained by each oscillator and then performs phasing addition processing for adjusting phase differences between the reception signals obtained by the oscillators and adding the reception signals to each other, to thereby form a reception beam. Further, the wave transmission/reception circuit 20 converts the reception signal from an analog signal into a digital signal and outputs the converted reception signal as an echo data string along a direction of the ultrasonic beam.

The ultrasonic beam is electronically scanned by electronic scanning of the oscillator array to form one scanning surface, and echo data of one frame is acquired from the scanning surface. The frame memory 22 stores an echo data string along the ultrasonic beam output from the wave transmission/reception circuit 20.

The ultrasonic wave image generation unit 42 is configured to convert a spatial coordinate system defining the echo data from a wave transmission/reception coordinate system (circular polar coordinate system), which is specified by the scanning direction of the ultrasonic beam and the depth of the beam direction, into a two-dimensional orthogonal coordinate system suitable for a scanning system of the display unit 30 configured to display a tomographic image, to thereby generate, for example, a B-mode image as a ultrasonic image corresponding to each scanning surface of the ultrasonic probes 10a and 10b. The ultrasonic image generation unit 42 may generate an ultrasonic image expressed in another mode, for example, an M-mode image.

The pulse generation circuit 24 is configured to generate and output a drive signal to the HIFU transducer 12 in accordance with the control by the control unit 40.

The moving mechanism control circuit 26 can control the moving mechanism 4 based on a control amount input from outside, and is configured to perform, for example, three-dimensional position control. For example, error information on a position to be followed and an HIFU focal point obtained from the ultrasonic image is input to the moving mechanism control circuit 26. The moving mechanism control, circuit 26 grasps the current position of the end effector 2 based on the value of an encoder of a motor of the moving mechanism 4 and determines a control amount to be output to the motor based on the positional information and the received error information. This control can be performed by, for example, proportional control (P control).

The control unit 40 is configured to control an operation of each unit of the ultrasound theragnostic system 1. For example, the control unit 40 controls the wave transmission/reception circuit 20 and the pulse generation circuit 24.

Further, the control unit 40 can input the position of the portion of interest obtained by the tracking processing unit 44 to the moving mechanism control circuit 26 and move the end effector 2, for example, in accordance with the movement of the affected part.

Regarding the affected part that moves in association with an organ, the tracking processing unit 44 is configured to follow the organ and grasp the position of the affected part through use of the positional relationship between the organ and the affected part. In this case, the tracking processing unit 44 captures a contour of the organ in a biological image and tracks the organ based on the contour. The tracking processing unit 44 searches for a contour of the organ for each biological image obtained in time series. With this, the organ tracking based on the contour by the tracking processing unit 44 is less liable to be influenced by deformation of the organ at the time of movement and can thus stably perform following, as compared to tracking through matching processing using templates each having a certain shape with respect to different biological images. Further, the amount of information obtained increases by basically performing a search over the entire contour of the organ. Accordingly, even when an acoustic shadow overlaps with a part of the organ and causes a defective portion of the contour, the organ tracking based on a contour by the tracking processing unit 44 allows the position and rotation angle of the organ to be easily estimated based on a non-defective portion of the contour.

The organ position estimation section 50 of the tracking processing unit 44 is configured to determine an estimated position of the organ of concern in the biological image obtained by photographing a biological structure based on the past movement of the organ of concern in vivo. The search for a contour in the tracking processing unit 44 described above can be performed, for example, by a method involving searching for points on a contour (contour points) along a plurality of directions set radially from a search center point set in the organ of concern. In this case, the organ position estimation section 50 determines, as the estimated position, for example, a point that is set to a search center point in a subsequent contour search in the organ contour estimation section 52. Further, in a method involving moving the past contour shape in accordance with the movement (translational movement and rotational movement) of the organ of concern and searching for new contour points, based on the contour after the movement, in a direction perpendicular to the contour, the contour after the movement can be determined by the organ posit ion estimation section 50. That is, in this case, the organ position estimation section 50 determines, as the estimated position, an arrangement of a contour at a movement destination to which the past contour has been moved or a contour point group forming the contour.

The organ contour estimation section 52 is configured to search for contour points of the organ of concern in a region corresponding to the position estimated by the organ position estimation section 50 in the biological image and determine an estimated contour of the organ of concern based on the contour points. For example, the region corresponding to the position estimated by the organ position estimation section 50 is a region on the periphery of the search center point when the search center point has been determined as the estimated position, and a region in the vicinity of the contour after the movement when the contour obtained by moving the past contour has been determined as the estimated position. The organ contour estimation section 52 discretely sets a plurality of control points in an active contour model (ACM) in a circumferential direction of the organ of concern and adjusts the position of each control point, to thereby search for the contour points that are positioned on the contour and represent a contour shape. A contour is formed of a line obtained by connecting the contour points corresponding to the control points, respectively, in the order of the control points along the circumferential direction of the organ. Specifically, the contour points are set so as to correspond to the positions of edges detected in the biological image.

An ACM method is one of methods of extracting a contour of an object from an image. In the ACM method, a closed curve to be the shape of an object is represented by a deformable shape model, and a contour is determined through use of an energy function that is defined to become minimum when the closed curve is matched with the contour of the object.

As the shape model, for example, there is given a model in which the shape of an object is reconstructed through use of several basis vectors (number of basis vectors: t) having large eigenvalues among basis vectors obtained by defining a previously measured contour or the like to be learning data and applying principal component analysis to the learning data. As the learning data, sample data acquired from the subject to be examined can be used. Further, the shapes of the same organ of concern have similarity even in different people, and hence it is also possible to create an average shape model that is generally applicable to humans, for example, through use of basis vectors extracted from learning data obtained by measuring a large number of people.

With the above-mentioned shape model, the contour shape of the organ is represented by a sum of a reference shape and a linear combination of a plurality of deformation modes that are linearly independent from each other. In this case, for example, the reference shape is given by an average shape of the learning data, and each deformation mode forming the linear combination is represented by the basis vectors selected in descending order of the eigenvalues. Specifically, each control point is defined as two-dimensional coordinates, and hence the contour shape can be represented by a vector formed of 2n elements, where n represents the number of the control points. Therefore, when $\xi$ represents a 2n-dimensional column vector indicating a contour shape to be estimated, u represents a 2n-dimensional column vector indicating an average shape of the learning data, V represents a matrix of 2n rows and t columns indicating deformation patterns corresponding to t deformation modes, and b represents a t-dimensional column vector formed of coefficients in the linear combination of the deformation modes, the contour can be expressed by the following expression in the above-mentioned shape model. The number t of the deformation patterns is determined, for example, so that a cumulative contribution ratio becomes 98%, $$\xi = u + Vb \tag{1}$$

As a procedure based on the shape model described above, there has been known an active shape model (ASM) method. Further, in P. Yan et al., "Discrete Deformable Model Guided by Partial Active Shape Model for TRUS Image Segmentation", IEEE Transactions on Biomedical Engineering, Vol. 57, pp. 1158-1166; 2010, as a procedure obtained by correcting the ASM method in conformity with the case in which a part of a contour of the organ becomes unclear in an ultrasonic image of a still image, a partial active shape model (PASM) method is described. In the PASM method, a contour is determined through use of only control points in which clear contour points have been obtained by a search among a plurality of control points to be set along the circumference of the organ. In this embodiment, the accuracy of an estimated contour is improved with respect to an acoustic shadow and the like through use of the PASM method. That is, the organ contour estimation section 52 determines coefficients in the linear combination of the deformation modes based only on control points corresponding to clear contour points having a degree of reliability greater than or equal to a predefined reference among the control points in the shape model represented by a sum of the reference shape and the linear combination of the deformation modes described above (PASM processing).

In the PASM method, a contour can be expressed by the following expression.

$$\xi_s = u_s + V_s b_s + \varepsilon_s \quad (2)$$

In the expression (2), $\xi_s$ and $u_s$ represent column vectors in which elements corresponding to unclear contour points are omitted in the vectors $\xi$ and u, respectively. Further, $V_s$ represents a matrix in which a row corresponding to the unclear contour points is omitted in the matrix V. $\varepsilon_s$ represents an approximation error caused by excluding the unclear contour points. $b_s$ represents a t-dimensional column vector formed of coefficients in the linear combination of the deformation modes and is determined so as to minimize the error $\varepsilon_s$.

Further, the organ, contour estimation section 52 corrects the shape model, which is obtained in the PASM processing, by a SNAKE method being one procedure of the ACM. That is, the organ contour estimation section 52 corrects the vector $\xi$ representing the positions of control points, which is obtained by substituting the coefficient vector $b_S$ determined in the PASM processing into the coefficient vector b of the expression (1), based on an energy minimizing principle regarding a contour shape through use of the SNAKE method.

Energy E is calculated, by an energy function defined by the following expression regarding a closed curve.

$$E = \alpha E_{cont} + \beta E_{curv} + \gamma E_{img} \quad (3)$$

In the expression (3), $E_{cont}$ represents an energy component in accordance with the length of the curve, $E_{curv}$ represents an energy component in accordance with the smoothness of the curve, and $E_{img}$ represents an energy component in accordance with edge intensity at a position of the curve, that is, a brightness gradient.

For example, when position vectors of pixels in a biological image corresponding to three adjacent control points are represented by $v_{i-1}$, $v_i$, and $v_{i+1}$, $E_{cont}$ can be defined by the following expression through use of a distance $|v_{i+1} - v_i|$ between two adjacent control points. In the following expressions (4) to (6), $\Sigma$ represents a total sum regarding i, that is, a sum regarding all the control points.

$$E_{cont} = \Sigma |v_{i+1} - v_1|^2 \quad (4)$$

The smoothness of the curve can be represented by second-order differentiation of the curve. As the absolute value of a second derivative value becomes smaller, it can be evaluated that the curve is smoother. Therefore, $E_{curv}$ can be defined by the following expression through use of an approximate value $(v_{i+1} - 2v_i + v_{i-1})$ of the second-order differentiation of the curve at a control point corresponding to a pixel having the position, vector $v_i$.

$$E_{curv} = \Sigma |v_{i+1} - 2v_1 + v_{i-1}|^2 \quad (5)$$

Further, when the brightness value of a control point corresponding to the pixel having the position vector is represented by I ($v_i$), and the maximum value and the minimum value of the brightness value at eight pixels in the vicinity of the position vector $v_i$ are $I_{max}$ and $I_{min}$, respectively, $E_{img}$ can be defined by the following expression.

$$E_{img} = -\Sigma \{I(v_i) - I_{min}\}/(I_{max} - I_{min}) \quad (6)$$

The symbols $\alpha$, $\beta$, and $\gamma$ represent coefficients for determining the weight of each energy component, and are set in advance based on experience and experiment. In a curve suitable as a contour, it can be expected that the length thereof is short, the way of bending is smooth, and the brightness gradient is large due to the matching with an edge. In view of the foregoing, $\alpha$, $\beta$, and $\gamma$ are set to $\alpha > 0$, $\beta > 0$, and $\gamma > 0$ with respect to the definitions of $E_{cont}$, $E_{curv}$, and $E_{img}$ in the expressions (4) to (6) so that the energy E becomes smaller in the above-mentioned suitable case.

The organ contour estimation section 52 searches for the contour points in terms of the estimated position of the organ of concern toy the organ position estimation section 50, and after that, calculates the coefficient vector $b_s$ based on the above-mentioned PASM method and corrects the contour shape corresponding to the coefficient vector $b_s$ by the SNAKE method. The processing based on the PASM method and the processing based on the SNAKE method are started with a clear contour point having a degree of reliability greater than or equal to the predefined reference among the contour points obtained as an initial value, and alternately repeated until a predetermined ending condition is satisfied, to thereby determine an estimated contour. The ending condition can be set to, for example, a condition that energy reaches a predetermined value or less, a condition that a reduction in energy settles, a condition that a change in contour settles, or a condition that the processing is reiterated a plurality of times.

The affected part tracking section 54 is configured to perform portion-of-interest tracking processing for determining a position of the affected part as the portion of interest in the biological image. In this processing, the affected part tracking section 54 determines the position of the portion of interest based on the estimated contour estimated by the organ contour estimation section 52 with reference to sample data acquired in advance regarding the positional relationship between the contour of the organ of concern and the portion of interest that moves in association with the organ of concern.

Along with the movement of the organ of concern in vivo, in general, the contour of the organ is deformed, and there is also a change in the positional relationship of the portion of interest, that moves in association with the organ with respect to the contour of the organ. The sample data is acquired prior to the main search for the portion of interest for treatment or the like. In this embodiment, the sample data is acquired from the ultrasonic image captured by using the ultrasonic probe 10, but may be acquired through use of another image diagnostic modality (e.g., X-ray photography, CT, MR, or PET). The sample data associates the contour shape of the organ with the position, of the portion of interest. The position of the portion of interest in this case is a position at which the displacement of the portion of interest caused by the movement of the organ has been removed, and is basically determined so as to exhibit the positional relationship with respect to the contour. The position of the portion of interest is represented by, for example, coordinates having a center of gravity of the contour as an origin.

The affected part tracking section 54 calculates a position of the portion of interest based on the contour estimated by the organ contour estimation, section 52 through use of a position model based on the assumption that there is a correlation between the contour shape ξ and the position of the portion of interest. The position model to be used in this embodiment represents the position of the portion of interest corresponding to a contour of interest, which is the contour at certain timing of interest among the contours to be deformed of the organ of concern, as a sum of the reference position and the linear combination of a plurality of displacement modes corresponding to the deformation modes.

Specifically, when the position vector of the portion of interest in the contour of interest is represented by a column vector donated by a symbol ρ, the vector u and the matrix V are determined based on the learning data and can be dealt with as constants in the expression (1). Therefore, a correlation can be assumed between the coefficient vector b and the position vector ρ based on the correlation between the contour ξ and the position vector ρ. In view of the foregoing, the position model can be formulated as the following expression through use of the coefficient vector b in the linear combination of each deformation mode in the shape model corresponding to the contour of interest as the coefficient in the linear combination of each displacement mode.

$$\rho = q + Wb \quad (7)$$

In the expression (7), q represents a column vector indicating the reference position. Further, W represents a matrix of 2 rows and t columns. Each column thereof represents a displacement vector in the displacement mode corresponding to each of the t deformation modes.

As the reference position q, an average position of the portion of interest based on the sample data can be used. The vector q can be dealt with as a constant. Further, the coefficient vector b is known regarding the estimated contour, and can thus be dealt with as a constant in the expression (7).

The matrix W representing the displacement mode can be obtained by applying the position model represented by the expression (7) to a plurality of sample data (number of sample data: m). Specifically, the expression (7) regarding each of the m sample data can be written as the following expression through use of a matrix P of 2 rows and m columns in which the column vector ρ regarding each sample data is arranged in m columns, a matrix Q of 2 rows and m columns in which the column vector q is repeatedly arranged in m columns, and a matrix B of t rows and m columns in which the column vector b regarding each sample data is arranged in m columns. In the following expression, an error is introduced. Further, it is preferred that data on the position of the portion of interest that has not been obtained due to the influence of an acoustic shadow or the like be removed from the sample data to be used in the configuration of the following expression.

$$P = Q + WB + \varepsilon_p \quad (8)$$

The matrix W is determined so as to minimize the error $\varepsilon_p$, and the affected part tracking section 54 calculates the position ρ of the portion of interest corresponding to the estimated contour ξ based on the coefficient vector b for the estimated contour ξ through use of the matrix w in the expression (7). The calculated position ρ is output to the control unit 40 and used for, for example, control of the end effector 2 in HIFU therapy.

The display image generation unit 46 is configured to generate a display image being an image suitable for monitoring or the like of the organ of concern or the affected part by a medical doctor, a laboratory technician, or other such person through the display unit 30 based on the ultrasonic image generated by the ultrasonic image generation unit 42. In this embodiment, when there is a defect and an unclear portion due to an acoustic shadow or the like in an image of the organ of concern in the ultrasonic tomographic image, the display image generation unit 46 generates an image in which the portion has been complemented.

The region-to-be-complemented setting section 60 of the display image generation unit 46 is configured to distinguish a clear region having a clear image quality from an unclear region having an unclear image quality based on a predetermined criteria in an image of the organ of concern appearing on the biological image and determine a region to be complemented formed of at least one polygon containing the unclear region and having the control points in a contour search as vertices. In this embodiment, an example in which a quadrangle is used as the polygon is described.

The image synthesis section 62 is configured to complement the unclear region through use of the biological image acquired after the start of tracking of the portion of interest and stored in the storage unit 34. The image synthesis section 62 reads out a portion of the clear region of the biological image stored in the storage unit 34, which corresponds to a quadrangle having, as vertices, control points common to those of the quadrangle of the region to be complemented, performs homography transformation of matching the read portion to the quadrangle of the region to be complemented, and synthesizes the biological image after the transformation of the portion with the region to be complemented. Another linear transformation, for example, affine transformation may be used instead of the homography transformation.

The display unit 30 is an image display device, for example, a liquid crystal display, and is configured to display biological images, for example, an ultrasonic image generated by the ultrasonic image generation unit 42 and a display image generated by the display image generation unit 46.

The input unit 32 is an input device, for example, a keyboard or a pointing device. The input unit 32 is operated by the medical doctor, the laboratory technician, or other such person, and used for operation instruction and data input to the ultrasound theragnostic system 1.

The storage unit 34 is configured to store various programs and various data to be used in the processors forming the arithmetic processing unit 28 and input or output the information with respect to the arithmetic processing unit 28. The storage unit 34 stores, for example, ultrasonic image data 70, sample data 72, a shape model 74, and a position model 76.

The ultrasonic image data 70 is data on a biological tomographic image generated by the ultrasonic image generation unit 42. For the purpose of diagnosis or the like, contour estimation of the organ and position estimation of the affected part by the tracking processing unit 44 maybe performed with respect to a previously photographed biological image. In this case, the ultrasonic image data 70 is stored in advance in the storage unit 34 and subjected to processing by the tracking processing unit 44.

Further, the ultrasonic image data 70 is used for complementing the unclear region in the processing by the display image generation unit 46. In this application, it is basically sufficient that data from present time to time before one movement cycle of the organ be stored as the ultrasonic image data 70. Further, for example, when a portion to be an unclear region is identified in advance from photographing in the past movement cycle, only an image in a frame containing this portion as a clear region may be recorded as the ultrasonic image data 70.

The sample data 72 is acquired from the subject to be examined as advance preparation for treatment or the like. Specifically, the medical doctor, the laboratory technician, or other such person acquires biological images at a plurality of timings in the movement cycle of the organ from the subject to be examined and determines the positional relationship between the contour of the organ of concern and the portion of interest that moves in association with the organ of concern in the biological images, and then stores the positional relationship in the storage unit 34 as the sample data 72.

The shape model 74 is a shape model described in the description of the organ contour estimation section 52. Specifically, the vector u and the matrix V in the expression (1) are determined in advance based on the learning data and stored in the storage unit 34 as the shape model 74.

The position model 76 is a position model described in the description of the affected part tracking section 54. Specifically, the vector q and the matrix W in the expression (7) are determined in advance based on the sample data and stored as the position model 76 in the storage unit 34.

Next, the operation and the like of the ultrasound theragnostic system 1 are described.

Figure 4:
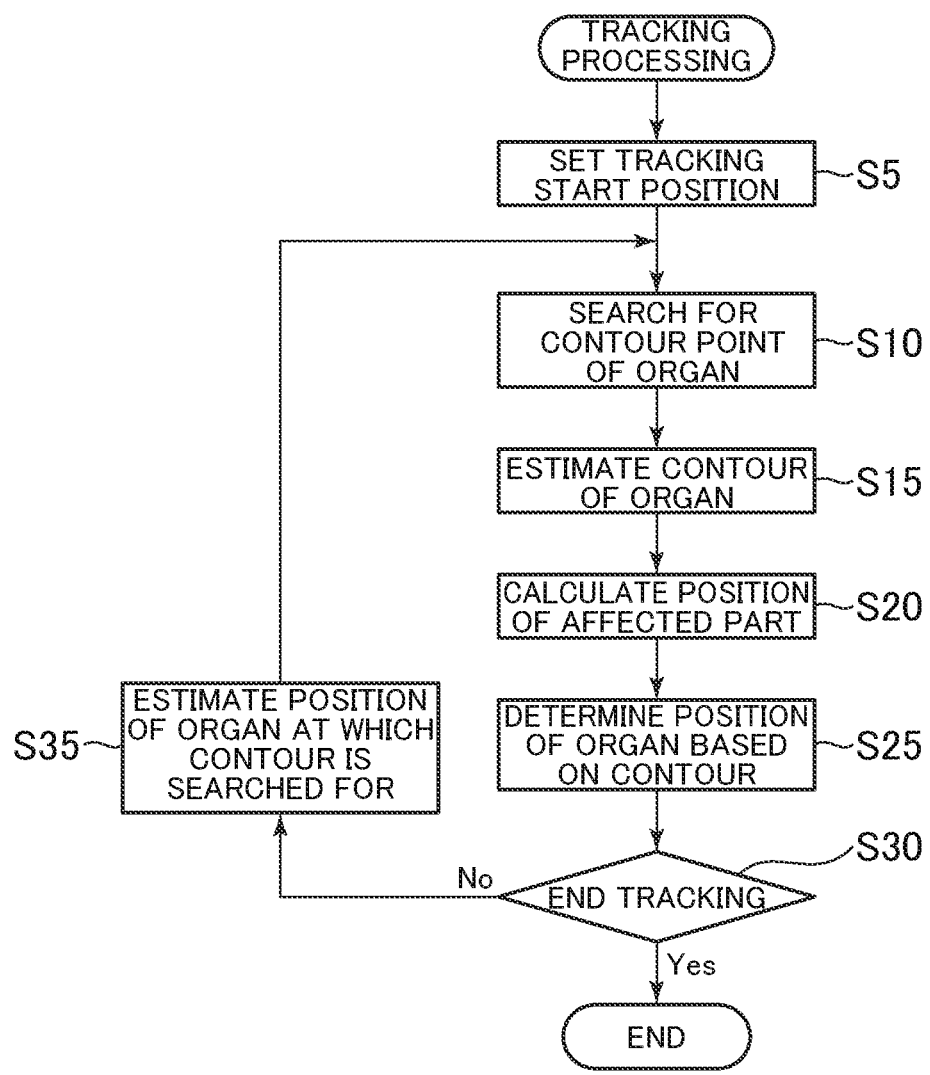
FIG. 4 is a schematic flow diagram of processing of tracking an affected part, which is performed by the ultrasound theragnostic system in the embodiment of the present invention.

FIG. 4 is a schematic flow diagram of processing of tracking an affected part, which is performed by the ultrasound theragnostic system 1. When the ultrasound theragnostic system 1 is activated, the ultrasound theragnostic system 1 starts generating an ultrasonic image as a biological image through use of the ultrasonic probe 10. For example, an operator can adjust the position of a subject to be examined or the position of the end effector 2 so as to track the affected part while monitoring the ultrasonic image obtained in real time. The operator sets an image position at certain, timing of an organ that moves together with the affected part as a tracking start position (Step S5). For example, the tracking start position can be defined as one point in the organ.

Next, the organ contour estimation section 52 searches for contour points with using the tracking start position as an estimated position of the organ (Step S10). As described above, as the method of searching for contour points, there are given a method of searching for contour points along a plurality of directions set radially from a search center point and a method of searching tor contour points in a direction perpendicular to a contour. Here, a configuration example using the former method is described, and the latter method is described later.

Figure 5:
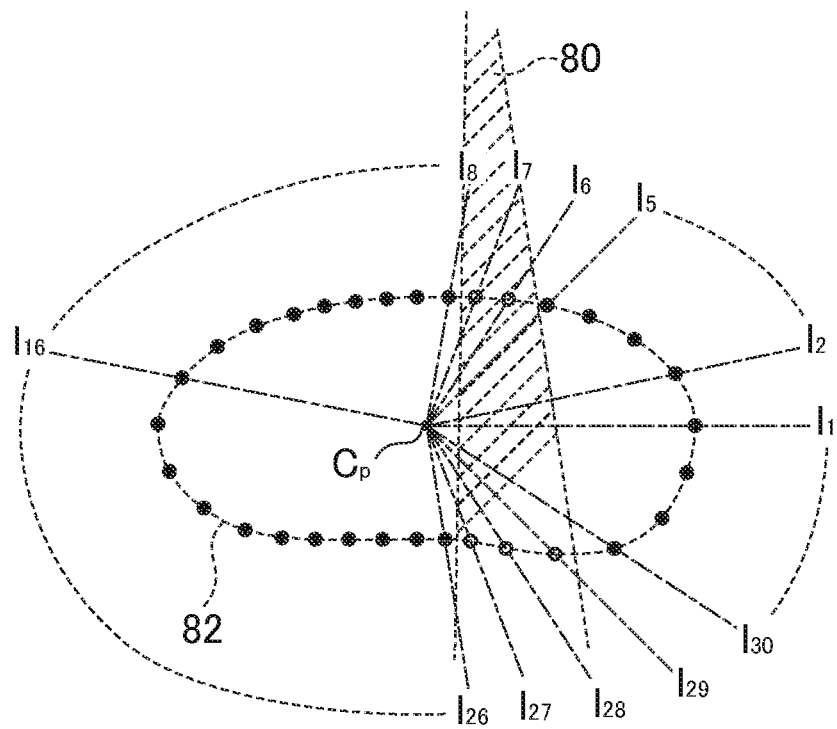
FIG. 5 is a schematic view of a biological image for illustrating a search for contour points, which is performed by an organ contour estimation section.

FIG. 5 is a schematic view of a biological image for illustrating a search for contour points. For example, the estimated position is defined by a point $C_P$ in the organ in the biological image, and the organ contour estimation section 52 searches for contour points along lines 1 set radially in a plurality of directions at equal angle intervals with the point $C_P$ being the search center point. The lines (search lines) for searching for the contour points are associated with control points. n search lines $1_1$ to $1_s$ are set, the number of the search lines being the same as that of the control points, and $1_i$ corresponds to a control point represented by a position vector $v_i$. Incidentally, since the search center point is set in the organ, the contour of the organ forms a closed curve surrounding the search center line.

In this embodiment, the contour points are searched for in 32 directions ($1_1$ to $1_{32}$), and the positions of edges (edge points) are detected as the contour points. In this case, the degree of reliability of each contour point can be determined based on edge intensity. That is, an edge having intensity of a predetermined threshold value or more can be detected as a clear contour point.

The organ contour estimation section 52 proceeds with an edge search, for example, in a direction farther away from the search center point (or in a direction approaching the search center point). For example, a brightness value is confirmed for each pixel from an inner side (or an outer side) to an outer side (or an inner side) of the organ along the search line 1, and a point at which the brightness value becomes equal or more than a threshold value for the first time is defined as a clear contour point. The search on the search line 1 can be started from any position on the search line 1, For example, the search can be started from the search center point. Meanwhile, in this search, a search range may foe limited to a range in which it is assumed that there is a contour point, and the search may be performed from an inner side (or an outer side) to an outer side (or an inner side) within this range. Through limitation of the search range, erroneous detection of a contour point can be reduced. For example, the search range can be set based on the size assumed as the organ.

For edge detection, the feature in which a brightness gradient of the biological image increases at an edge is used, and specifically, an edge can be detected through use of a well-known edge detection filter. In FIG. 5, clear contour points are indicated by the marks "●". Meanwhile, there may be directions in which contour points, are not identified due to an acoustic shadow or the like. For example, in FIG. 5, points (indicated by the marks "o") at which the search lines $1_6$, $1_7$, and $1_{27}$ to $1_{23}$ and a contour 82 of the organ cross each other are positioned in an acoustic shadow region 80, and hence those points become unclear contour points having small edge intensity, with the result that those points are not detected as the contour points by the organ contour estimation section 52.

Figure 6:
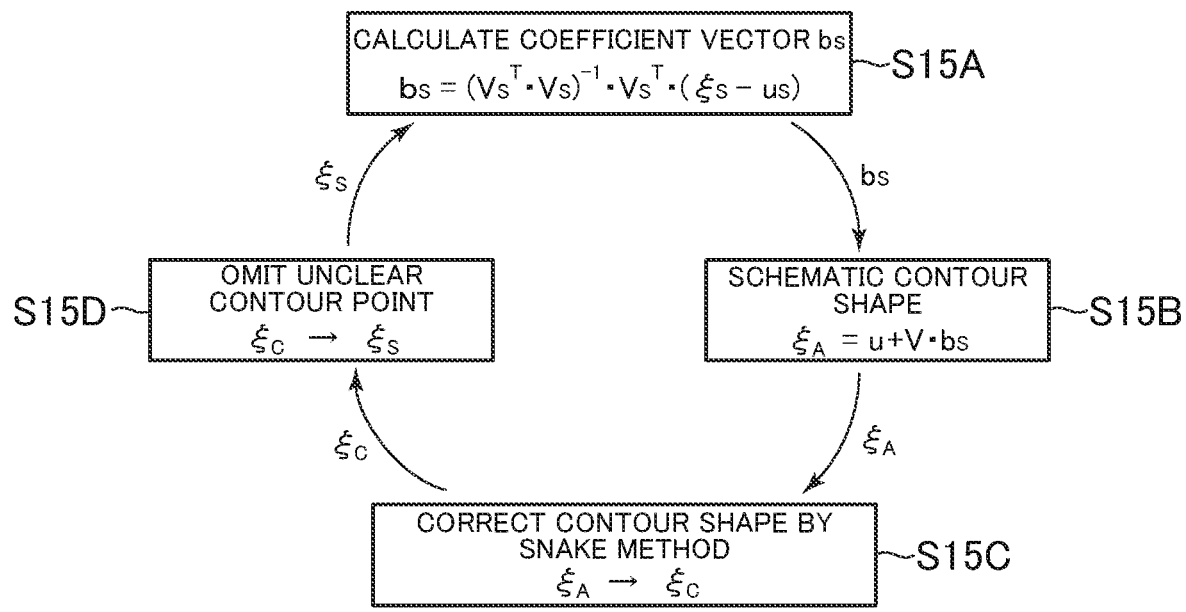
FIG. 6 is a schematic diagram for illustrating a procedure for estimating a contour shape, which is performed by the organ contour estimation section.

The organ, contour estimation section 52 calculates a schematic contour shape of the organ based on the above-mentioned PASM method and corrects the schematic contour shape by the SNAKE method through use of the detected organ contour points, to thereby determine an estimated contour of the organ (Step S15). FIG. 6 is a schematic diagram for illustrating this procedure in Step S15.

The organ contour estimation section 52 calculates a coefficient vector $b_S$ corresponding to a vector $\xi_S$ formed of coordinates of the detected contour points (Step S15A). The coefficient vector $b_S$ in the expression (2) based on the PASM method can be determined so as to minimize the square $|\varepsilon_S|^2$ of a norm of an error vector by a least squares method. That is, the coefficient vector $b_S$ chat gives min $|\xi_S - u_S - V_S b_S|^2$ for the vector $\xi_S$ is determined. Specifically, the coefficient sector $b_S$ can be calculated by the following expression.

$$b_S = (V_S^T V_S)^{-1} V_S^T (\xi_S - u_S) \tag{9}$$

When the coefficient vector $b_S$ given by the expression (9) is substituted into the expression (1), an approximate vector $\xi_A$ of the contour shape $\xi$ is obtained as a schematic, contour shape of the organ (Step S15B).

$$\xi_A = u + V b_S \tag{10}$$

Here, the approximate vector $\xi_A$ is a 2n-dimensional vector formed of coordinates of all the control points. That is, the approximate vector $\xi_A$ also gives the positions of the control points at which the contour points have not been detected in Step S10 due to an acoustic shadow or the like.

The organ contour estimation section 32 determines a shape $\xi_C$ obtained by correcting the schematic contour shape $\xi_A$ by the above-mentioned SNAKE method (Step S15C). Then, the organ contour estimation section 52 regenerates the vector $\xi_S$ with the elements corresponding to the unclear contour points being omitted in the vector $\xi_C$ (Step S15D), and the flow returns to Step S15A of determining the coefficient vector $b_S$ by the expression (9). The organ contour estimation section 52 repeats the cycle including Steps S15A to S15D until a predetermined ending condition is satisfied, to thereby determine the obtained vector $\xi_C$ as the estimated contour $\xi$.

The affected part tracking section 54 substitutes the coefficient vector $b_s$ corresponding to the estimated contour $\xi$ determined, by the organ contour estimation section 52 into the expression (7), to thereby calculate a position ρ of the affected part corresponding to the estimated contour $\xi$ (Step S20).

Here, as described above, the matrix W in the expression (7) is determined by the expression (8) based on the sample data. Specifically, the matrix W can be determined so as to minimize the square $|\varepsilon_P|^2$ of a norm of an error matrix by the least squares method. That is, the matrix W that gives min $|P-Q-WB|^2$ for the sample data is determined. Specifically, the matrix W can be calculated by the following expression.

$$W^T=(BB^T)^{-1}B(P^T-Q^T) \quad (11)$$

The position ρ of the affected part calculated by the affected part tracking section 54 is output to the control unit 40 and used for control in treatment or the like using the HIFU transducer 12.

Further, in the ultra sonic image generated by the ultrasonic image generation unit 42 or the display image generated by the display image generation unit 46, the position ρ of the affected part having a marker or the like synthesized therewith can be displayed on the display unit 30. In particular, in an acoustic shadow region, an image of the affected part is not obtained or is difficult to be determined, and hence affected part tracking on an image by the operator becomes easier by showing the calculated position ρ in the biological image.

Meanwhile, the organ contour estimation section 52 determines the position of the organ corresponding to the estimated contour $\xi$ (Step S25). For example, the center of gravity of the estimated, contour $\xi$ can be determined to be the position of the organ.

When the tracking processing unit 44 is not instructed to end the tracking processing ("No" in Step S30), the tracking processing unit 44 calculates an estimated position of the organ at a time to subsequently determine the position of the affected part with the organ position estimation section 50 (Step S35), and the processing in Steps S10 to S25 by the organ contour estimation section 52 and the affected part tracking section 54 is repeated. The time interval for determining the position of the affected part can be basically set appropriately within a range which is equal to or more than a frame cycle of the biological image and in which stable tracking can be performed.

As described above, the organ position estimation section 50 determines the estimated position of the organ based on the past movement of the organ. For example, the organ position estimation section 50 can calculate the center of gravity of the estimated contour as the position of the organ in Step S25 and predict the center of gravity of the contour as the position of the organ at a subsequent time based on a velocity vector of the organ determined based on the positions of the organ at the latest two times. Alternatively, the organ position estimation section 50 may determine a track of the position of the organ by tracking in advance preparation for treatment or the like and predict a new position on the track based on the past position and the speed of the organ. Further, coordinates regarding the rotational movement in addition to coordinates regarding the translational movement can also be predicted as the position based on the past movement.

Further, in Step S10, the predicted center of gravity of the contour determined to be the position of the organ can be used as the search center point $C_P$ of the contour points. The predicted center of gravity is less liable to be placed outside the organ and hence is suitable as the search center point. Thus, the organ position estimation section 50 predicts the positron that has been displaced by the movement of the organ and searches for the contour points of the organ in a region corresponding to the position, thereby stable tracking can be performed even when the speed of the organ is high.

Meanwhile, when the speed of the organ is low or when the time interval for tracking is short, for example, it can be expected that the center of gravity of the contour determined at a certain time exists in the organ at a subsequent time. Therefore, the center of gravity at the certain time may be used as the search center point of the contour points at the subsequent time. Further, immediately after the start of the tracking processing, there may be a case in which the position of the organ cannot be estimated based on the past movement. However, even in such case, the current position of the organ can be approximately determined to be the estimated position of the organ at the subsequent time.

Figure 7:
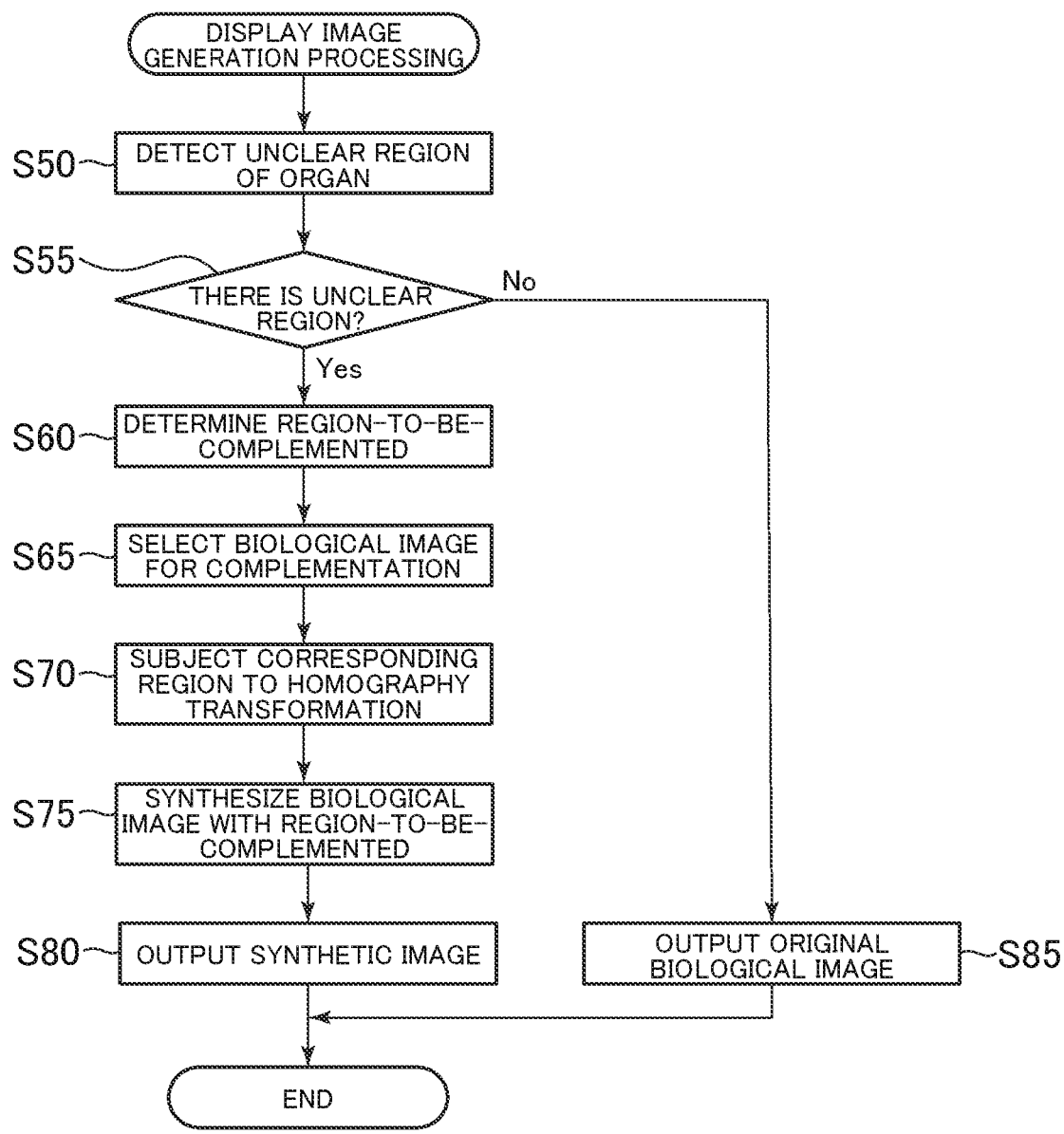
FIG. 7 is a schematic flow diagram of display image generation processing performed by the ultrasound theragnostio system in the embodiment of the present invention.

FIG. 7 is a schematic flow diagram of display image generation processing performed by the ultrasound theragnostic system 1. In the ultrasound theragnostic system 1, an ultrasonic tomographic image is generated as a biological image by the ultrasonic image generation unit 42, and the ultrasonic tomographic image can be displayed on the display unit 30. Meanwhile, when there is a defect and an unclear portion due to an acoustic shadow or the like in an image of the organ of concern in the ultrasonic tomographic image obtained by the ultrasonic image generation unit 42, the display image generation unit 46 generates an image in which the portion has been complemented.

The region-to-be-complemented setting section 60 of the display image generation unit 46 acquires the ultrasonic image (referred to as "original biological image" in the sense that the image has not been subjected to image synthesis processing described later) generated by the ultrasonic image generation unit 42, and distinguishes an unclear region having an unclear image quality from the other clear region in the image of the organ (Step 350).

For example, the region-to-be-complemented setting section 60 detects an unclear region in a region on an inner side of the estimated contour $\xi$ determined by the organ contour estimation section 52. For example, an acoustic shadow is formed in a band shape behind the rib or the like when viewed from the ultrasonic probe 10, and when the organ overlaps with the band-shaped region, the contour of the over lapping portion becomes unclear. Therefore, the unclear region can be detected based on the control points determined to correspond to the unclear contour points by the organ contour estimation section 52. For example, the region-to-be-complemented setting section 60 detects the unclear contour points in the contour of the organ and separates the unclear contour points, by using the center of gravity of the contour as a reference position, into points on an upper side close to the ultrasonic probe 10 and points on a lower side far away from the ultrasonic probe 10. Then, in a portion on the upper side of the contour, a pair of clear contour points sandwiching a section in which the unclear contour points exist is determined, and similarly in a portion on the lower side of the contour, a pair of the clear contour points sandwiching a section in which unclear contour points exist are determined. A quadrangle having, as vertices, four clear contour points forming the pair of the clear contour points on the upper side and the pair of the clear contour points on the lower side, which are determined as described above, is defined as an unclear region.

Figure 8A:
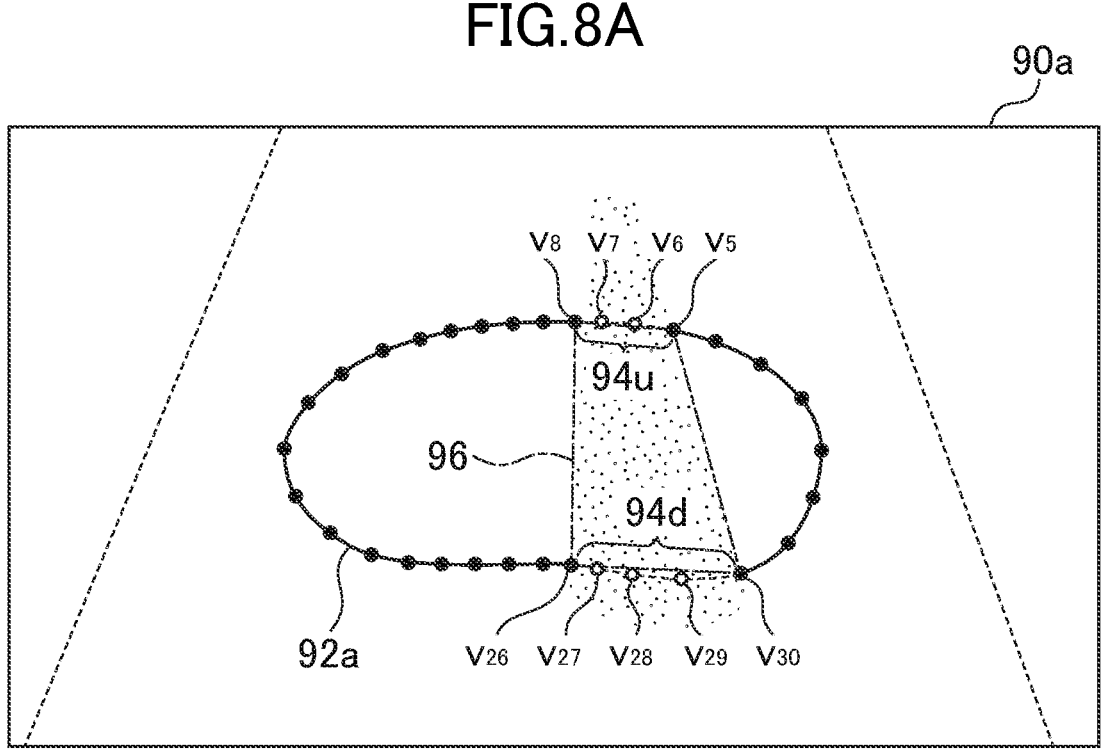
FIG. 8A is a schematic view for illustrating processing performed by a region-to-be-complemented setting section.
Figure 8B:
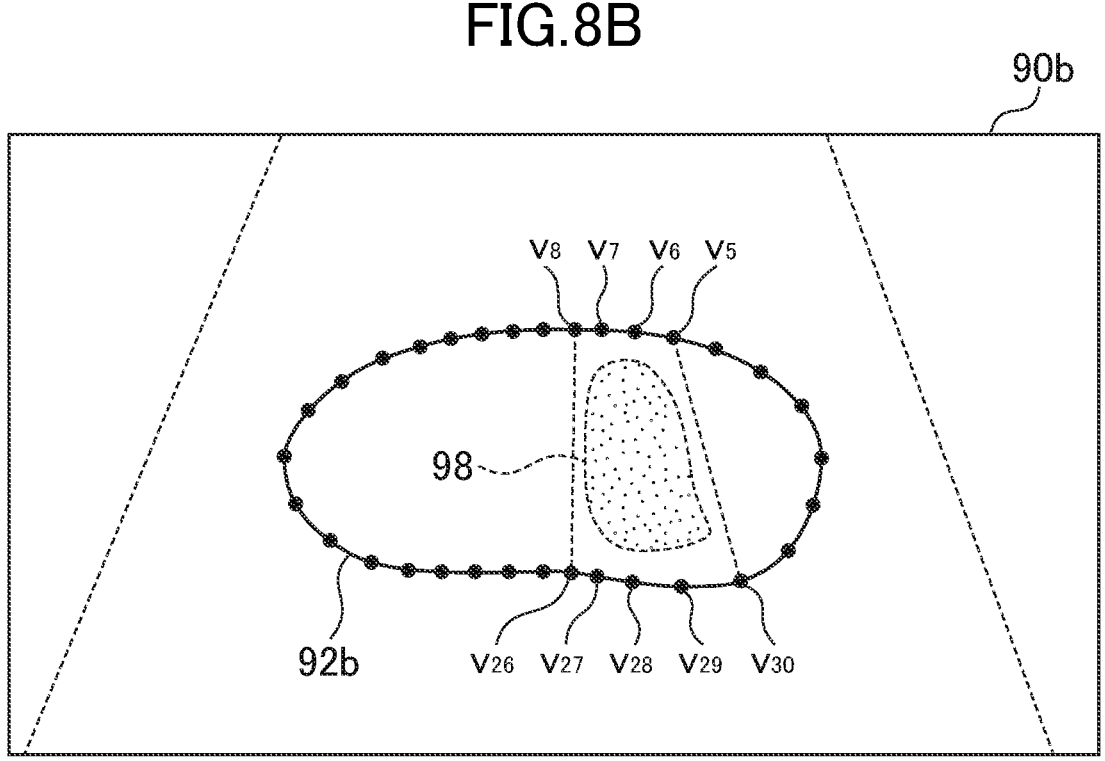
FIG. 8B is a schematic view for illustrating the processing performed by the region-to-be-complemented setting section.

FIG. 8A and FIG. 8B are each a schematic diagram for illustrating processing performed by the region-to-be-complemented setting section 60. FIG. 8A is a diagram for illustrating a specific example of estimation, of an unclear section based on the unclear section of the contour described above. When a contour point (control point) on the search line $1_k$ is represented by $v_k$, $v_6$ and $v_7$ and $v_{27}$ to $v_{29}$ are unclear contour points in an ultrasonic tomographic image 90a. In an organ contour 92a, a section 94u sandwiched between clear contour points $v_6$ and $v_8$ and a section 94d sandwiched between clear contour points $v_{26}$ and $v_{30}$ are detected as sections each having an unclear contour. The region-to-be-complemented setting section 60 estimates a region sandwiched between the section 94u and the section 94d to be an unclear region. Specifically, the region-to-be-complemented setting section 60 performs approximation of defining a quadrangle 96, which has, as vertices, the contour points $v_5$, $v_8$, $v_{26}$, and $v_{30}$ at both ends of the sections 94u and 94d, as an unclear region.

Further, when the region-to-be-complemented setting section 60 determines an unclear region of the organ caused by an acoustic shadow, the region-to-be-complemented setting section 60 can impose the following condition on two unclear sections, or the section in which unclear contour points continue on the upper side of the contour and the section in which unclear contour points continue on the lower side of the contour: The two unclear sections are those which cross a common straight line passing through the ultrasonic probe 10. The region-to-be(tm)-complemented setting section 60 estimates that two unclear sections satisfy the condition are contour portions facing each other in a portion of the organ overlapping with the acoustic shadow. Also in this case, the region-to-be-complemented setting section 60 determines the pair of clear contour points described above for each of the two contour potions, and a region of a quadrangle having, as vertices, four clear contour points forming the two pairs is defined as an unclear region. In the example of FIG. 8A, the sections 94u and 94d are arranged in a line with the ultrasonic probe 10 (not shown in FIG. 8A) positioned above the ultrasonic tomographic image 90a in FIG. 8A. Thus, FIG. 8A is also an illustration of an example of processing under the condition that the sections of unclear contour points on the upper side and the lower side and the ultrasonic probe 10 are arranged, in a straight line, Further, the above-mentioned unclear region may be a peripheral region outside of a field of view of an ultrasonic image apparatus. The region-to-be-complemented setting section 60 can also detect the unclear region based on an image indicator of the biological image. For example, a region in which contrast is less than a predefined threshold value may be defined as the unclear region. FIG. 8B is an illustration of a specific example of this case. In this example, a region 98 is determined to be an unclear region due to low contrast in an organ contour 92b of an ultrasonic tomographic image 90b.

Further, the unclear region may be determined through use of both the above-mentioned estimation based on an unclear section of a contour and the estimation based on an image indicator. For example, in the example of FIG. 8A, the quadrangle 96 can be determined to be the unclear region after it is confirmed that the quadrangle 96 includes the region in which contrast is less than a threshold value.

When the unclear region is detected ("Yes" in Step S55), the region-to-be-complemented setting section 60 determines a region to be complemented formed of at least one quadrangle that includes the unclear region and has control points as vertices (Step S60).

For example, in the above-mentioned estimation based on an unclear section of a contour, the quadrangle (quadrangle 96 in the example of FIG. 8A) determined to be the unclear region is determined to be the region to be complemented. Further, in the unclear region 98 of FIG. 8B, for example, one quadrangle $v_5v_8v_{26}v_{30}$, which is the same as the quadrangle 96 of FIG. 8A, can also be determined to the region to be complemented, or three quadrangles that can be formed through use of the control points $v_5$ to $v_8$ and $v_{26}$ and $v_{30}$ being the unclear contour points, that is, a quadrangle $v_5v_6v_{29}v_{30}$, a quadrangle $v_6v_7v_{28}v_{29}$, and a quadrangle $v_7v_8v_{26}v_{28}$ can also be determined to be the region to be complemented.

Figure 9:
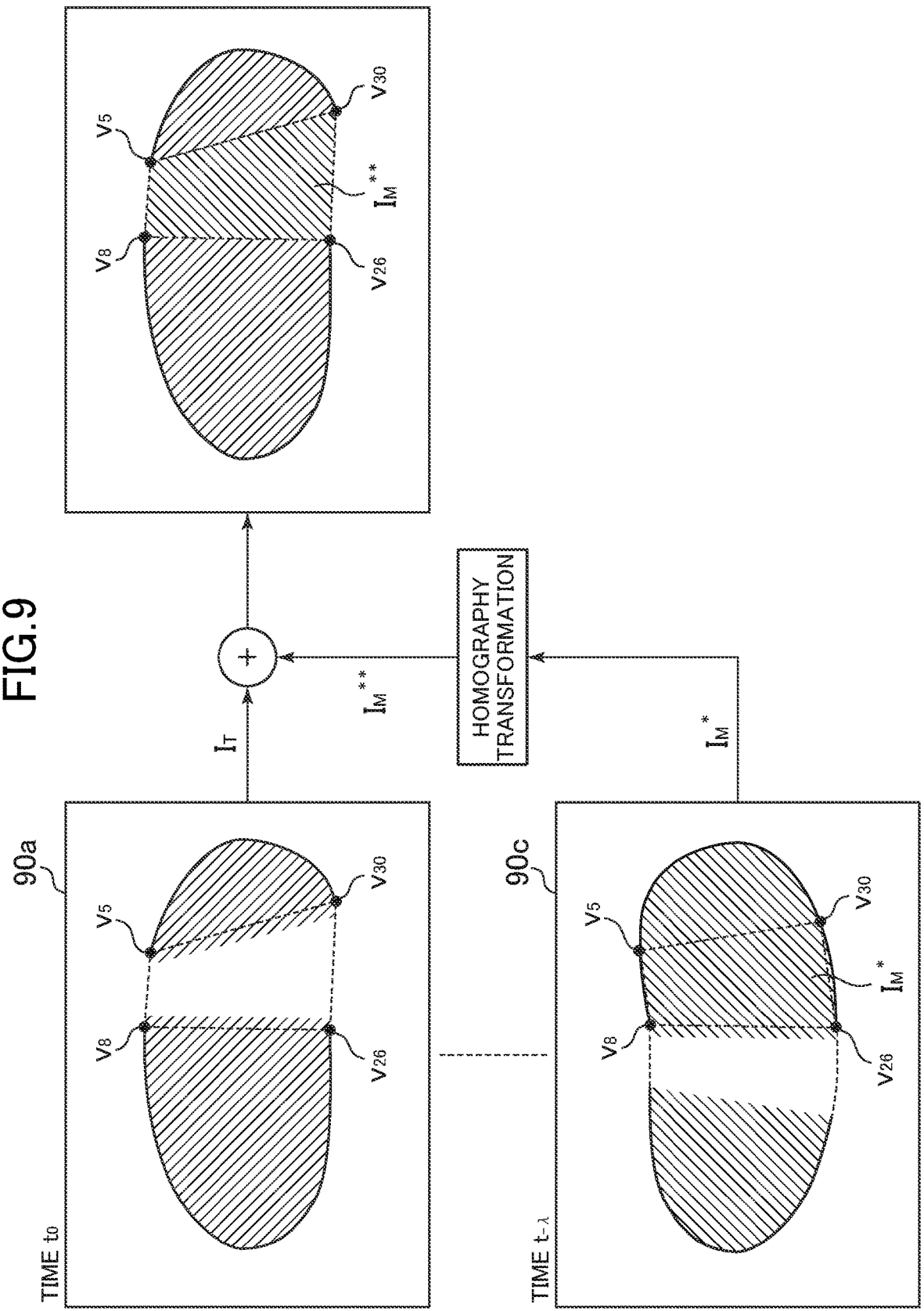
FIG. 9 is a schematic view for illustrating processing performed by an image synthesis section.

When the region to be complemented is determined, the image synthesis processing is performed by the image synthesis section 62. FIG. 9 is a schematic view for illustrating processing performed by the image synthesis section 62, and a processing example corresponding to the example of FIG. 8A is illustrated in. FIG. 9.

The image synthesis section 62 reads out, as a biological image for complementation, a biological image in a quadrangle having, as vertices, control points common to those of a quadrangle in the region to be complemented in the clear region from the ultrasonic image data 70 of the storage unit 34, which serves as biological image storage means (Step S65).

It is preferred that the biological image to be used for complementation (hereinafter represented by a symbol "$I_M$") be basically close to a biological image having a detected unclear region (hereinafter represented by a symbol "$I_T$") in terms of photographing time. The image synthesis section 62 searches for images in which a region of the ultrasonic image, which corresponds to the region to be complemented in the biological image $I_T$, is a clear region, for example, in the order from the newest ultrasonic images accumulated in the ultrasonic image data 70 prior to the ultrasonic image being the biological image $I_T$, and selects a first found image as the biological image $I_M$. Then, the image synthesis section 62 reads out a portion corresponding to the region to be complemented in the biological image $I_M$ of one frame as a biological image for complementation (hereinafter represented by a symbol "$I_M^+$") from the ultrasonic image data 70.

In FIG. 9, as the biological image $I_T$ at time $t_0$, the ultrasonic tomographic image 90a of FIG. 8A is illustrated, and a region to be complemented is a quadrangle having, as vertices, the control points $v_5$, $v_8$, $v_{26}$, and $v_{30}$. The image synthesis section 62 selects an ultrasonic tomographic image 90c at time $t_{-A}$, which is the time immediately before the region to be complemented enters am acoustic shadow region, as the biological image $I_M$ with respect to the biological image $I_T$. Then, the image synthesis section 62 reads out the image data in the quadrangle having, as vertices, the control points $v_5$, $v_8$, $v_{26}$, and $v_{30}$ in the ultrasonic tomographic image 90c as the biological image $I_M^+$ for complementation from the ultrasonic image data 70.

The image synthesis section 62 performs homography transformation of matching the biological image $I_M^+$ for complementation to the quadrangle of the region to be complemented (Step S70). That is, in the example of FIG. 9, an image of the quadrangle $v_5 v_8 v_{26} v_{30}$ in the ultrasonic tomographic image 90c is selected as the biological image $I_M^+$ and is subjected to projective transformation into the quadrangle $v_5 v_8 v_{26} v_{30}$ in the ultrasonic tomographic image 90a. Then, the image synthesis section 62 synthesizes a biological image (represented by a symbol "$I_M^{+\ast}$") obtained by subjecting the biological image $I_M^+$ to projective transformation with the region to be complemented of the ultrasonic tomographic image 90a being the biological image $I_T$ (Step S75). Then, the synthetic image generated in Step S75 is output to the display unit 30 (Step S80).

Meanwhile, when the unclear region has not been detected in Step S50 ("No" in Step S55"), it is determined that complementation processing for an image is not required, and the display image generation unit 46 outputs the original biological image input from the ultrasonic image generation unit 42 to the display unit 30 (Step S85).

The ultrasound theragnostic system 1 can repeat the display image generation processing together with the processing of tracking the affected part.

As described above, as the method of searching for contour points in the tracking processing, there are given a method of searching for contour points along a plurality of directions set radially from a search center point and a method of searching for contour points in a direction perpendicular to a contour. In the above-mentioned embodiment, the tracking processing is mainly described by exemplifying the former method. Next, the case of performing the tracking processing by the latter method is described.

In this case, the organ contour estimation section 52 predicts a contour of the organ at the estimated position based on the past estimated contour and searches for contour points along a direction orthogonal to the predicted contour. Specifically, in Step S10 of FIG. 4, the organ contour estimation section 52 acquires a contour assumed at a tracking start position as a reference contour and performs initial setting of control points on the reference contour. It is only necessary that the reference contour be approximate to a contour at the position and time at the tracking start.

After the tracking processing is started, and Steps S10 to S25 are performed, a contour at the most recent time is obtained. Therefore, the contour can be arranged at the estimated position in Step S35 and used as the reference contour. As described above, the estimated position is not limited to coordinates regarding the translational movement and encompasses coordinates regarding the rotational movement.

Meanwhile, immediately after the start of the tracking processing, the reference contour can be set based on the sample data or the like.

For example, the organ contour estimation section 52 sets, as initial positions of the control point, intersections between the plurality of lines 1 set radially from the center of gravity of the reference contour and the reference contour. The plurality of lines 1 are set at equal angle intervals in the same manner as in the lines 1 defined to be the search lines in the above-mentioned configuration example. Meanwhile, the search direction of a contour point is set to a direction that passes through the initially set control point and is perpendicular to the reference contour, in place of the direction along the line 1. Specifically, a normal vector $n=(n_x, n_y)$ directed from an inner side to an outer side of the reference contour is defined at each of the initially set control points. Then, the control point is moved on a straight line (represented by a symbol "$1_n$") along the normal vector to search for a clear contour point. For example, brightness values of a biological image are taken out on an inner side and an outer side of the control point, respectively, for m pixels and defined as a normal vector profile (NVP). Specifically, in the biological image, coordinates of the control point are represented by $(x_c, y_c)$, and a brightness value of a pixel corresponding to coordinates $(x_i, y_i)$ (where i is an integer of $1 \leq i \leq 2m$) in the following expression is represented by $f_i$. The NVP is defined by a 2m-dimensional vector $f=[f_1, f_2, \ldots, f_{2m}]^T$.

$$(x_i, y_i) = (x_C + (i-m)n_x, y_C + (i-m)n_y)$$

The brightness value of an i-th pixel from the inner side is $f_i$. That is, $f_1$ to $f_m$ are brightness values of pixels on the inner side of the control point, and $f_{m+1}$ to $f_{2m}$ are brightness values of pixels on the outer side of the control point.

As an indicator for determining whether or not the set control point is a clear contour point, for example, c defined by the following expression is calculated through use of an inner product of the vectors p and f.

$$c = p^T \cdot f / 2m$$

In this expression, p represents a 2m-dimensional vector defined in accordance with the feature of a change in brightness value on the inner side and the outer side of the clear contour point along the straight line $1_n$. For example, in an ultrasonic image obtained when the organ of concern is the prostate gland, on the premise that the brightness increases from the inner side to the outer side of the contour in the vicinity of the contour, for example, p is expressed as follows: $p=[1, \ldots 1, -1, \ldots -1]^T$ in which values of the first element to the m-th element corresponding to the pixels on the inner side of the control point are 1, whereas values of the (m+1)-th element to the 2m-th element corresponding to the pixels on the outer side are $-1$, A clear contour point is determined when $c < -1$.

For example, the organ contour estimation section 52 moves the control point in a direction (inner direction and outer direction) farther away from the initial control point along the straight line $1_n$ and calculates c being an indicator value to determine the control point, at which the indicator value c satisfying the condition of the clear contour point is obtained and which is closest to the initial control point, as a new contour point. In the same manner as in the processing described above regarding a search along the search line 1, the search range, that is, the movement range of the control point may be limited to a range in which it is assumed that there is a contour point, and the search may be performed from the inner side to the outer side within the range.

The method of searching for contour points in a direction orthogonal to the reference contour has an effect in which a change in brightness at an interface between the image of the organ and the acoustic shadow when the organ overlaps with the acoustic shadow is less liable to be erroneously detected as a contour point.

Modification Example

In the above-mentioned embodiment, the case in which the biological image is a two-dimensional image formed by an ultrasonic echo is described. However, the biological image is not limited thereto. For example, the biological image may be a stereo image, that is, a three-dimensional image. Further, as a procedure for searching for a biological structure to form an image, various procedures can be used. For example, the present invention can also be applied through use of, as a biological image, a two-dimensional image or a three-dimensional image formed by X-ray fluoroscopy, computed tomography (CT), magnetic resonance imaging (MRI), and positron emission tomography (PET).

The present invention has a feature of tracking a tissue and a body part that move substantially periodically in vivo, and there is no limitation on the types or a diagnostic apparatus and a treatment apparatus for which this technology is used.

For example, when the present invention is applied to radiation external therapy that is one of non-invasive therapy other than the above-mentioned HIFU therapy, a treatment system configured to apply radiation while following the movement of an affected part can be constructed, and localized radiation to the affected part is enabled, with the result that a therapeutic effect can be enhanced with fewer side effects. Also in cutting-edge cancer therapy, such as proton therapy, heavy particle therapy, and neutron therapy, a system similar to that described above can be constructed.

Further, when a signal detected from a living body is weak, for example, in PET, long-term imaging is performed. In such case, a biological image having a blur suppressed can be acquired by moving a detector while following a site of interest and performing electronic movement compensation of the obtained biological image data that changes with time through use of the technology of tracking a site of interest in the present invention.

For example, when HIFU is irradiated while an affected part is followed, there is a problem in that pain is caused in a subject to be examined when HIFU hits the rib while an organ of the affected part passes through a rear side of the rib. In the present invention, the accuracy of following of the affected part is improved, and hence it is easy to suitably perform treatment control for weakening HIFU at timing at which the affected part is hidden by the rib and irradiating HIFU so as to avoid the rib. Further, at a place close to the main blood vessel, the diaphragm, and the digestive tract in which the irradiation accuracy of an error of 1 mm or less is required, in order to avoid damage to those body parts, treatment control for weakening the intensity of HIFU and narrowing a focus region is preferred. With tracking of an affected part in the present invention, the timing at which the affected part is hidden by an acoustic shadow can be grasped, and hence this feature enables such treatment control.

While there have been described what are at present considered to be certain embodiments of the invention, it will be understood that various modifications may be made thereto, and it is intended that the appended claims cover all such modifications as fail within the true spirit and scope of the invention.

What is claimed is:

1. An in vivo movement tracking apparatus, comprising:
   at least one processor; and
   at least one storage device configured to store a plurality of instructions,
   the plurality of instructions causing, when being executed by the at least one processor, the at least one processor to perform:
      organ position estimation processing for determining an estimated position of an organ of concern in a biological image, which is obtained by photographing a biological structure, based on a past movement of the organ of concern in vivo;
      contour estimation processing for searching for contour points of the organ of concern in a region corresponding to the estimated position in the biological image and determining an estimated contour of the organ of concern based on the contour points; and
      portion-of-interest tracking processing for determining a position of a portion of interest, which moves in association with the organ of concern, in the biological image based on the estimated contour with reference to previously acquired sample data regarding a positional relationship between a contour of the organ of concern and the portion of interest,
   the contour estimation processing including:
      searching for the contour points corresponding to a plurality of control points, respectively, in an active contour model having a contour shape of the organ of concern; and
      determining the estimated contour by using a shape model, the shape model representing the contour shape with a sum of a reference shape and a linear combination of a plurality of deformation modes that are linearly independent from each other, and a clear contour point having a degree of reliability greater than or equal to a predefined reference among the contour points being an initial value, the estimated contour being determined by alternately repeating PASM processing for determining a coefficient of each of the plurality of deformation modes in the linear combination based only on the control point corresponding to the clear contour point among the plurality of control points and processing for correcting a position of the control point given by the PASM processing by a SNAKE method, which is based on an energy minimizing principle regarding the contour shape, and
   the portion-of-interest tracking processing including, in a position model representing the position of the portion of interest corresponding to a contour of interest of the organ of concern with a sum of a reference position and a linear combination of a plurality of displacement modes corresponding to the plurality of deformation modes:
      setting an average position of the portion of interest, which is based on the sample data, as the reference position;
      setting the coefficient in the linear combination of each of the plurality of deformation modes in the shape model corresponding to the contour of interest as a coefficient in the linear combination of each of the plurality of displacement modes;
      setting the plurality of displacement modes obtained by applying the position model to the sample data; and
      determining the position of the portion of interest corresponding to the estimated contour through use of the position model.

2. The in vivo movement tracking apparatus according to claim 1, wherein the contour estimation processing includes predicting the contour at the estimated position based on the estimated contour in the past and searching for the contour points along a direction orthogonal to the predicted contour.

3. The in vivo movement tracking apparatus according to claim 1, wherein the at least one storage device is configured to further store:
   the biological image; and
   a plurality of instructions for causing, when being executed by the at least one processor, the at least one processor to perform:

region-to-be-complemented setting processing for distinguishing a clear region having a clear image quality from an unclear region having an unclear image quality based on a predetermined criteria in an image of the organ of concern appearing on the biological image and determining a region to be complemented, which is formed of at least one polygon containing the unclear region and having the control points as vertices; and image synthesis processing for reading out, from the at least one storage device, the biological image in a polygon that is contained in the clear region and has, as vertices, the control points common to the control points of the at least one polygon in the region to be complemented, and subjecting the read biological image in the polygon to linear transformation to match the read biological image in the polygon to the at least one polygon in the region to be complemented, to thereby synthesize the biological image subjected to the linear transformation with the region to be complemented.

* * * * *